(12) United States Patent
Hoeffkes et al.

(10) Patent No.: US 6,620,408 B2
(45) Date of Patent: Sep. 16, 2003

(54) BLEACHING COMPOSITION

(75) Inventors: Horst Hoeffkes, Duesseldorf (DE); Winifried Neuhaus, Duesseldorf (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

(21) Appl. No.: 10/176,557

(22) Filed: Jun. 21, 2002

(65) Prior Publication Data

US 2003/0012751 A1 Jan. 16, 2003

Related U.S. Application Data

(63) Continuation of application No. PCT/EP00/12658, filed on Dec. 13, 2000.

(30) Foreign Application Priority Data

Dec. 22, 1999 (DE) .......................... 199 61 934

(51) Int. Cl.⁷ .............................. A61K 7/135
(52) U.S. Cl. .................... 424/62; 424/70.1; 424/70.19; 424/70.22; 424/70.31
(58) Field of Search .................. 424/70.1, 62, 70.19, 424/70.22, 70.31

(56) References Cited

U.S. PATENT DOCUMENTS 5,989,530 A    11/1999  Lorenz et al.

FOREIGN PATENT DOCUMENTS

| DE | 38 14 356 | 9/1988 |
| DE | 196 00 216 | 6/1996 |
| EP | 0 560 088 | 8/1994 |
| WO | WO 97/39726 | 10/1997 |

*Primary Examiner*—Jyothsan Venkat
(74) *Attorney, Agent, or Firm*—Stephen D. Harper; Gregory M. Hill

(57) ABSTRACT

A powder or paste form preparation for bonding human hair based on at least one solid peroxo compound and at least one solid alkalizing agent characterized in that they contain a dicarboxylic acid or ester thereof of the formula (I)

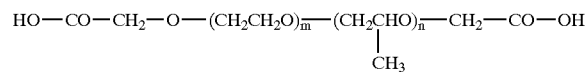

Wherein m and n are independently 0, 1 or 2.

3 Claims, No Drawings

BLEACHING COMPOSITION

CROSS REFERENCE TO RELATED APPLICATIONS

This application is a continuation under 35 U.S.C. §365(c) and 35 U.S.C. §120 of international application PCT/EP00/12658, filed on Dec. 13, 2000, the international application not being published in English. This application also claims priority under 35 U.S.C. §119 to DE 199 61 934.4 filed on Dec. 22, 1999.

BACKGROUND OF THE INVENTION

This invention relates to a preparation in the form of a powder or paste for blonding human hair.

Changing the shape and color of the hair is an important area of modern cosmetics. In this way, the appearance of the hair can be adapted both to the latest fashion trends and to the individual requirements of the consumer. Permanent wave processes and other processes which change the shape of hair may be used virtually irrespective of the hair to be treated. By contrast, coloring processes and particularly blonding processes are limited to certain starting hair colors. Thus, only light brown to medium-brown hair is suitable for lightening processes, so-called blonding processes. The basic principles of blonding processes are known to the expert and are comprehensively described in relevant monographs, for example by K. Schrader in "Grundlagen und Rezepturen der Kosmetika", 2nd Edition, 1989, Dr. Alfred Hüthig Verlag, Heidelberg, and by W. Umbach (Ed.) in "Kosmetik", 2nd Edition, 1995, Georg Thieme Verlag, Stuttgart/New York.

For blonding human hair, particularly for so-called tress application, solid or paste-form preparations are normally mixed with a dilute hydrogen peroxide solution immediately before use. The resulting mixture is applied to the hair and then rinsed out after a certain contact time.

The preparations mentioned, which are normally mixed with a hydrogen peroxide solution before use, are referred to hereinafter as "blonding preparations". All quantities mentioned relate exclusively to these preparations, unless otherwise stated.

Neither the paste-form nor the powder-form blonding preparations presently available on the market can be regarded as optimal. Although their blonding effect on the hair is satisfactory, they are still attended by various disadvantages and problems both at the production level and from the handling perspective. In the case of paste-form preparations which are made highly viscous on stability grounds, dosing and mixing behavior in the hydrogen peroxide solution are still unsatisfactory. Dust behavior is another problem in the production of pastes. In the case of powder-form products, dust behavior both during production and in use and mixing behavior in use are the focus of efforts at improvement.

It is proposed in EP-B1-0 560 088, for example, to improve the dust behavior of blonding powders by addition of oils or liquid waxes. In addition, it is proposed in German patent application DE-A1-196 00 216 to use special ethers in quantities of 4 to 20% by weight, based on the blonding powder as a whole, for de-dusting. Blonding pastes are described in DE-A1-38 14 356 for avoiding dust emission during processing.

It has now surprisingly been found that blonding preparations with excellent dust behavior and other advantageous properties can be obtained providing they contain certain dicarboxylic acids.

SUMMARY OF THE INVENTION

Accordingly, the present invention relates to powder-form or paste-form preparations for blonding human hair based on at least one solid peroxo compound and at least one solid alkalizing agent, characterized in that they contain a dicarboxylic acid corresponding to formula (I):

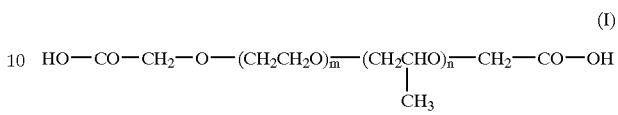

(I)

where m and n independently of one another stand for 0, 1 or 2, or esters thereof.

DETAILED DESCRIPTION OF THE INVENTION

The blonding preparations according to the invention contain a solid peroxo compound as a first compulsory component. Basically, the choice of this peroxo compound is not subject to any restrictions. Standard peroxo compounds known to the expert are, for example, ammonium peroxydisulfate, potassium peroxydisulfate, sodium peroxydisulfate, ammonium persulfate, potassium persulfate, sodium persulfate, potassium peroxydiphosphate, percarbonates, such as magnesium percarbonate, peroxides, such as barium peroxide, and perborates, urea peroxide and melamine peroxide. Of these peroxo compounds, which may also be used in combination, the inorganic compounds are preferred for the purposes of the invention. The peroxydisulfates, especially combinations of at least two peroxydisulfates, are particularly preferred.

The peroxo compounds are present in the blonding preparations according to the invention in quantities of preferably 20 to 80% by weight and more preferably 40 to 70% by weight.

The blonding preparations according to the invention contain an alkalizing agent to establish the alkaline pH of the mixture applied as a second compulsory component. According to the invention, the usual alkalizing agents known to the expert for blonding preparations, such as ammonium, alkali metal and alkaline earth metal hydroxides, carbonates, hydrogen carbonates, hydroxycarbonates, silicates, more particularly metasilicates, and alkali metal phosphates, may be used. In one preferred embodiment, the blonding preparations according to the invention contain at least two different alkalizing agents. Mixtures of, for example, a metasilicate and a hydroxycarbonate can be preferred.

The blonding preparations according to the invention contain alkalizing agents in quantities of preferably 10 to 30% by weight and more preferably 15 to 25% by weight.

According to the invention, the third compulsory component of the blonding preparations is a dicarboxylic acid corresponding to formula (I) or an ester thereof, a compound of formula (I) where m=2 and n=0, 3,6,9-trioxaundecanedioic acid, being particularly preferred. Mixtures of several dicarboxylic acids may also be used.

The blonding preparations according to the invention contain the dicarboxylic acid corresponding to formula (I) in a quantity of preferably 1 to 10% by weight.

In addition, it has been found to be of advantage for the powder-form preparations according to the invention to contain nonionic surfactants. Surfactants with an HLB value of 5.0 or higher are preferred. A definition of the HLB value can be found in Hugo Janistyn, "Handbuch der Kosmetika und Riechstoffe", Vol. III: Die Körperpflegemittel, 2nd Edition, Dr. Alfred Hüthig Verlag Heidelberg, 1973, pages 68–78 and Hugo Janistyn, "Taschenbuch der modernen Parfümerie und Kosmetik", 4th Edition, Wissenschaftliche Verlagsgesellschaft m.b.H. Stuttgart, 1974, pages 466–474 and the original works cited therein.

Substances which are commercially available in pure form as solids or liquids are particularly preferred nonionic surfactants because they are easy to process. The definition of purity in this connection does not relate to chemically pure compounds. Instead, mixtures of various homologs, for example with different alkyl chain lengths as are obtained in products based on natural fats and oils, may be used, particularly in the case of products on a natural basis. Even with alkoxylated products, mixtures with different degrees of alkoxylation are normally present. "Purity" in this connection rather relates to the fact that the substances selected should preferably be free from solvents, antiflow additives and other impurities.

Preferred nonionic surfactants are:

alkoxylated fatty alcohols containing 8 to 22 and more particularly 10 to 16 carbon atoms in the fatty alkyl group and 1 to 30 and preferably 1 to 15 ethylene oxide and/or propylene oxide units. Preferred fatty alkyl groups are, for example, lauryl, myristyl, cetyl and stearyl, isostearyl and oleyl groups. Particularly preferred compounds of this class are, for example, lauryl alcohol containing 2 to 4 ethylene oxide units, oleyl and cetyl alcohol containing 5 to 10 ethylene oxide units, cetyl and stearyl alcohol containing 10 to 30 ethylene oxide units and mixtures thereof and the commercial product Aethoxal® B (Henkel), a lauryl alcohol containing 5 ethylene oxide and 5 propylene oxide units. Besides the usual alkoxylated fatty alcohols, so-called "end-capped" compounds may also be used in accordance with the invention. In these compounds, the alkoxy group does not terminate in an OH group, but is "end-capped" in the form of an ether, more particularly a $C_{1-4}$ alkyl ether. One example of such a compound is the commercial product Dehypon® LT 054, a $C_{12-18}$ fatty alcohol+4.5 ethylene oxide butyl ether.

alkoxylated fatty acids containing 8 to 22 and more particularly 10 to 16 carbon atoms in the fatty acid group and 1 to 30 and more particularly 1 to 15 ethylene oxide and/or propylene oxide units. Preferred fatty acids are, for example, lauric, myristic, palmitic, stearic, isostearic and oleic acid.

alkoxylated, preferably propoxylated and more preferably ethoxylated mono-, di- and triglycerides. Examples of preferred compounds are glycerol monolaurate+20 ethylene oxide and glycerol monostearate+20 ethylene oxide.

polyglycerol esters and alkoxylated polyglycerol esters. Preferred compounds of this class are, for example, poly(3)glycerol diisostearate (commercial product: Lameform® TGI (Henkel)) and poly(2)glycerol polyhydroxy stearate (commercial product: Dehymuls® PGPH (Henkel)).

sorbitan fatty acid esters and alkoxylated sorbitan fatty acid esters such as, for example, sorbitan monolaurate and sorbitan monolaurate+20 ethylene oxide (EO).

alkyl phenols and alky phenol alkoxylates containing 6 to 21 and more particularly 6 to 15 carbon atoms in the alkyl chain and 0 to 30 ethylene oxide and/or propylene oxide units. Preferred representatives of this class are, for example, nonylphenol+4 EO, nonylphenol+9 EO, octyl phenol+3 EO and octyl phenol+8 EO.

Particularly preferred classes of nonionic surfactants are the alkoxylated fatty alcohols, the alkoxylated fatty acids and the alkyl phenols and alkyl phenol alkoxylates.

Preparations according to the invention containing nonionic surfactants in quantities of 0.5 to 10% by weight have been found to be particularly advantageous.

In addition, the blonding preparations according to the invention may contain any of the active principles, additives and auxiliaries typically present in such preparations. In many cases, they contain at least one surfactant. In principle, both anionic and zwitterionic, ampholytic and cationic surfactants are suitable. In many cases, however, it has proved to be of advantage to select the surfactants from anionic, cationic or nonionic surfactants. Anionic surfactants can be particularly advantageous.

Preferred anionic surfactants are alkyl sulfates, ether carboxylic acid salts containing 10 to 18 carbon atoms in the alkyl group and up to 12 glycol ether groups in the molecule, such as $C_{12}H_{25}$—$(C_2H_4O)_6$—$CH_2$—COONa and, more particularly, salts of saturated and especially unsaturated $C_{8-22}$ carboxylic acids, such as oleic acid, stearic acid, isostearic acid and palmitic acid.

These anionic surfactants should preferably be present in solid form, more particularly powder form. Soaps solid at room temperature, more particularly sodium stearate, are most particularly preferred. These soaps are present in quantities of preferably 5 to 20% by weight and more preferably 10 to 15% by weight.

Suitable nonionic surfactants are, in particular, $C_{8-22}$ alkyl mono- and oligoglycosides and ethoxylated analogs thereof. The nonethoxylated compounds in particular, which are also commercially available in powder form, have proved to be especially suitable.

Examples of the cationic surfactants suitable for use in the hair treatment preparations according to the invention are, in particular, quaternary ammonium compounds. Preferred quaternary ammonium compounds are ammonium halides, such as alkyl trimethyl ammonium chlorides, dialkyl dimethyl ammonium chlorides and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. Other cationic surfactants suitable for use in accordance with the invention are the quaternized protein hydrolyzates.

Alkyl amidoamines, particularly fatty acid amidoamines, such as the stearyl amidopropyl dimethyl amine obtainable as Tego Amid® S 18, are distinguished not only by their favorable conditioning effect, but also by their ready biodegradability.

Quaternary ester compounds, so-called "esterquats", such as the distearoyl ethyl hydroxyethyl ammonium methosulfate marketed under the name of Dehyquart® F 75 in admixture with cetearyl alcohol, are also readily biodegradable.

The compounds containing alkyl groups used as surfactants may be single compounds. In general, however, these compounds are produced from native vegetable or animal raw materials so that mixtures with different alkyl chain lengths dependent upon the particular raw material are obtained.

Other active substances, auxiliaries and additives are, for example,

- nonionic polymers such as, for example, vinyl pyrrolidone/vinyl acrylate copolymers, polyvinyl pyrrolidone and vinyl pyrrolidone/vinyl acetate copolymers and polysiloxanes,
- cationic polymers, such as quaternized cellulose ethers and other compounds stable and commercially obtainable as solids,
- zwitterionic and amphoteric polymers stable and preferably commercially obtainable as solids,
- anionic polymers such as, for example, polyacrylic acids, crosslinked polyacrylic acids and vinyl acetate/crotonic acid copolymers providing they are stable and preferably commercially obtainable as solids,
- thickeners, such as agar agar, guar gum, alginates, xanthan gum, gum arabic, karaya gum, locust bean gum, linseed gums, dextrans, cellulose derivatives, for example methyl cellulose, hydroxyalkyl cellulose and carboxymethyl cellulose, starch fractions and derivatives, such as amylose, amylopectin and dextrins, clays such as, for example, bentonite or fully synthetic hydrocolloids such as, for example, polyvinyl alcohol,
- structurants, such as glucose, maleic acid and lactic acid,
- hair-conditioning compounds, such as phospholipids, for example soybean lecithin, egg lecithin and kephalins, and also silicone oils,
- protein hydrolyzates, more particularly elastin, collagen, keratin, milk protein, soybean protein and wheat protein hydrolyzates, condensation products thereof with fatty acids and quaternized protein hydrolyzates,
- perfume oils, dimethyl isosorbide and cyclodextrins,
- dyes for coloring the preparations,
- active principles, such as panthenol, pantothenic acid, allantoin, pyrrolidone carboxylic acids and salts thereof,
- cholesterol,
- fats and waxes, such as spermaceti, beeswax, montan wax, paraffins,
- fatty alcohols and fatty acid esters,
- fatty acid alkanolamides,
- complexing agents, such as EDTA, NTA and phosphonic acids,
- swelling and penetration agents, such as carbonates, hydrogen carbonates, guanidines, ureas and primary, secondary and tertiary phosphates.

The expert will choose these other substances according to the desired properties of the preparations.

In another embodiment, the preparations according to the invention may contain oils and liquid waxes as care components in small quantities which should not exceed 2% by weight if the hair is not to be excessively weighted. Oils in this context are the known fatty and synthetic oils, but not perfume oils which may of course be used in small quantities as fragrances.

The powder-form preparations according to the invention may be produced by the standard methods known to the expert.

In one preferred method, the inorganic components present as solids are introduced first, optionally after mixing, for example in a Drais mixer, and sprayed with the surfactant. This is preferably done at room temperature, i.e. at temperatures below about 30° C. Elevated temperatures will only be applied when the dust-binding components selected are not liquid at those temperatures.

Another method of producing the preparations according to the invention is to grind all the components in a ball mill, for example in a centrifugal ball mill, a ring-roll mill or, more particularly, a spindle mill.

Finally, the powder-form preparations can be produced by mixing all the components and then treating the resulting mixture in a fluidized bed, preferably at elevated temperature depending on the solvent used.

For use on the hair, the blonding preparations according to the invention are mixed with a hydrogen peroxide solution immediately before application. The concentration of this hydrogen peroxide solution is determined on the one hand by legal requirements and, on the other hand, by the desired effect. 6% to 12% solutions in water are generally used. The quantity ratios of blonding preparation and hydrogen peroxide solution are normally in the range from 1:1 to 1:2, an excess of hydrogen peroxide solution being selected in particular when not too pronounced a blonding effect is required.

EXAMPLES

Six blonding preparations with the compositions shown in % by weight in Table 1 were prepared. In Examples A1 to A5, various blonding preparations were dedusted with different contents of 3,6,9-trioxaundecanoic acid. Example V is a comparison preparation with no dicarboxylic acid.

All the preparations except comparison preparation V were dust-free.

When mixed with a 6% developer (the commercial product "Poly Brilliance") in a ratio of 1:1, all the preparations gave homogeneous mixtures in a short time (comparison preparation V was mixed in a ratio of 0.92:1).

Dark blond hair tresses (Fischbach+Miller, Code 6923) weighing ca. 0.5 g were blonded for 30 minutes with ca. 2 g of blonding preparation. This was followed by a visual evaluation in comparison with formulations which did not contain any dedusting agent. No adverse effect on the lightening performance of the preparations according to the invention was observed.

TABLE 1

| Components | A1 | A2 | A3 | A4 | A5 | C |
|---|---|---|---|---|---|---|
| Ammonium peroxydisulfate | 56.5 | — | — | — | — | — |
| Potassium peroxydisulfate | — | 56.5 | 56.5 | — | — | 57.4 |
| Sodium peroxydisulfate | — | — | — | 56.5 | 46.5 | — |
| Sodium metasilicate | 18.0 | 18.0 | 18.0 | 18.0 | 18.0 | 19.4 |
| Magnesium hydroxycarbonate | 3.0 | 3.0 | 3.0 | 3.0 | 3.0 | 3.2 |
| Sodium chloride | 5.0 | 4.0 | 5.0 | 1.0 | — | 2.2 |
| Potassium sulfate | — | — | — | — | 10.0 | — |
| Sodium stearate | 11.0 | 11.0 | 11.0 | 11.0 | 11.0 | 11.8 |
| Pyrogenic silicon dioxide | 2.5 | 2.5 | 2.5 | 2.5 | 2.5 | 2.7 |
| Disodium dihydrogen ethylenediamine tetraacetate | 1.0 | 1.0 | 1.0 | 1.0 | 1.0 | 1.1 |
| 3,6,9-trioxaundecanedioic acid | 1.0 | 2.0 | 5.0 | 7.0 | 8.0 | — |
| Trisodium phosphate | 2.0 | 2.0 | — | — | — | 2.2 |
| Total quantity | 100 | 100 | 100 | 100 | 100 | 100 |

What is claimed is:

1. A method for blonding hair which comprises admixing a composition comprising at least one solid peroxo compound, at least one solid alkalizing agent and at least one dicarboxylic acid the formula

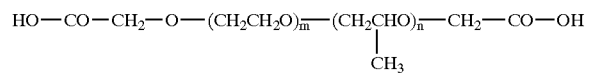

(I)

where m and n are independently 0, 1 or 2 with a hydrogen peroxide solution and applying said mixture to the hair to be treated.

2. The method of claim 1 wherein the composition and the hydrogen peroxide solution are in a ratio of from 1:1 to 1:2.

3. The method of claim 2 wherein said hydrogen peroxide solution contains 6% to 12% hydrogen peroxide.

* * * * *

UNITED STATES PATENT AND TRADEMARK OFFICE
CERTIFICATE OF CORRECTION

PATENT NO. : 6,620,408 B2
DATED : September 16, 2003
INVENTOR(S) : Hoeffkes et al.

It is certified that error appears in the above-identified patent and that said Letters Patent is hereby corrected as shown below:

Column 7,
Line 5, after "acid", insert -- of --.

Signed and Sealed this

Twenty-third Day of November, 2004

JON W. DUDAS
*Director of the United States Patent and Trademark Office*